(12) United States Patent
Tasker et al.

(10) Patent No.: US 6,219,929 B1
(45) Date of Patent: Apr. 24, 2001

(54) APPARATUS FOR ASSESSING AND MEASURING FOOT AND LOWER LIMB ABNORMALITIES

(76) Inventors: John Edwin Tasker, 178 Holyhead Road, Wellington, Telford, TF1 2DW; Mark John Price, 5 Boyden Close, Penkridge, Staffordshire, ST19 5TG, both of (GB)

( * ) Notice: Subject to any disclaimer, the term of this patent is extended or adjusted under 35 U.S.C. 154(b) by 0 days.

(21) Appl. No.: 09/339,310

(22) Filed: Jun. 23, 1999

(30) Foreign Application Priority Data

Jun. 27, 1998 (GB) .................................................. 9813833

(51) Int. Cl.⁷ .................................................. A61B 5/103
(52) U.S. Cl. .............................. 33/515; 33/512; 600/592; 600/595
(58) Field of Search .............................. 33/511, 512, 515, 33/549, 101; 600/592, 595; 73/862.045

(56) References Cited

U.S. PATENT DOCUMENTS

| | | | |
|---|---|---|---|
| 2,043,187 | * | 6/1936 | Owens .................................. 600/592 |
| 2,535,787 | * | 12/1950 | Darby .................................... 33/515 |
| 3,192,627 | * | 7/1965 | Levitt et al. ............................ 33/515 |
| 3,931,680 | * | 1/1976 | Greensides .............................. 33/3 B |
| 5,080,109 | * | 1/1992 | Arme, Jr. ................................ 33/515 |
| 5,168,634 | * | 12/1992 | Misevich ................................ 33/515 |
| 5,360,015 | * | 11/1994 | Heurte ................................... 128/779 |
| 5,435,320 | * | 7/1995 | Seitz ..................................... 128/782 |
| 5,572,569 | * | 11/1996 | Benoit et al. ......................... 378/209 |
| 5,645,516 | * | 7/1997 | Foster .................................... 482/79 |
| 5,897,464 | * | 4/1999 | Mcleod .................................. 482/79 |
| 5,979,067 | * | 11/1999 | Waters ................................... 33/512 |

FOREIGN PATENT DOCUMENTS

2312754 * 5/1997 (GB) ..................................... 33/3 C

* cited by examiner

Primary Examiner—Jacob K. Ackun, Jr.
Assistant Examiner—Faye Francis
(74) Attorney, Agent, or Firm—Andrus, Sceales, Starke & Sawall

(57) ABSTRACT

An apparatus for assesing and measuring, in tee dimensions, foot and lower limb abnormalities for example as shown in FIG. 1 comprises a rear plate intended to support a rear part of a patient's foot, in use, the rear plate being pivotable in both the frontal and sagittal planes, and a front plate intended to support a front part of the patient's foot, the front plate being pivotable in the frontal plane independently of the rear plate.

7 Claims, 4 Drawing Sheets

APPARATUS FOR ASSESSING AND MEASURING FOOT AND LOWER LIMB ABNORMALITIES

This invention relates to an apparatus suitable for use in assessing and measuring, in three dimensions, foot and lower limb abnormalities, and in particular to an apparatus permitting such assessment and measurement of foot and lower limb abnormalities a weight bearing (closed chain) position.

GB 2312754 describes a known apparatus for measuring foot and lower limb abnormalities which comprises a plate which is pivotally mounted upon a support structure. In use, a patient stands with one foot upon the plate, his other foot being supported by an appropriately sized step or the like. The pivot axis of the plate extends longitudinally of the plate such that the plate is pivotable in the frontal plane. The angle of the plate is adjusted until the patient's foot is properly supported. The angle of the plate is measured by measuring the displacement of markings drawn onto the patient's skin, and this information is used in the manufacture of an orthosis suitable for use by the patient. The plate may also be pivotable in the sagittal plane to permit measurement of the flexion of the ankle joint.

Such an apparatus is of relatively limited use, and it is an object of the invention to provide an apparatus permitting accurate assessment and measurement of foot and lower limb abnormalities.

According to the present invention there is provided an apparatus for assessing and measuring, in three dimensions, foot and lower limb abnormalities comprising a rear plate intended to support a rear part of a patient's foot, in use, the rear plate being pivotable in both the frontal and sagittal plan, and a front plate intended to support a front part of the patient's foot, the front plate being pivotable in the frontal plane independently of the rear plate.

The independently pivotable rear plate enables measurements to be made of movement of the sub-talar joint, typical prior arrangements measuring movement of the ankle joint, not the sub-talar joint.

The apparatus conveniently further comprises means for locking the front and rear plates and means permitting measurement of the angles of the front and rear plates.

As the apparatus of the invention permits measurement of the angle of the front plate independently of the rear plate, a clearer, more accurate assessment of a variety of abnormalities can be achieved. In particular, measurement of the positions of the patient's rearfoot and forefoot relative to the neutral or relaxed position of the sub talar and mid tarsal joints can be achieved when in a weight bearing (closed chain) position.

The invention will farther be described, by way of example, with reference to the accompanying drawings, in which.

The apparatus illustrated in the accompanying drawings comprises a base plate 10 of generally rectangular form, the upper surface of which is provided with a pair of longitudinally extending guide rails 12 which are spaced apart from one another. The guide rails 12 act to support a pair of adjustable foot support arrangements, each of the foot support arrangements including a base plate 14, 16 of dimensions suitable for being received by the guide rails 12 to permit sliding movement of the support arrangements in the longitudinal direction of the base plate 10. The guide rails 12 substantially prevent lateral movement of the support arrangements.

Figure 1:
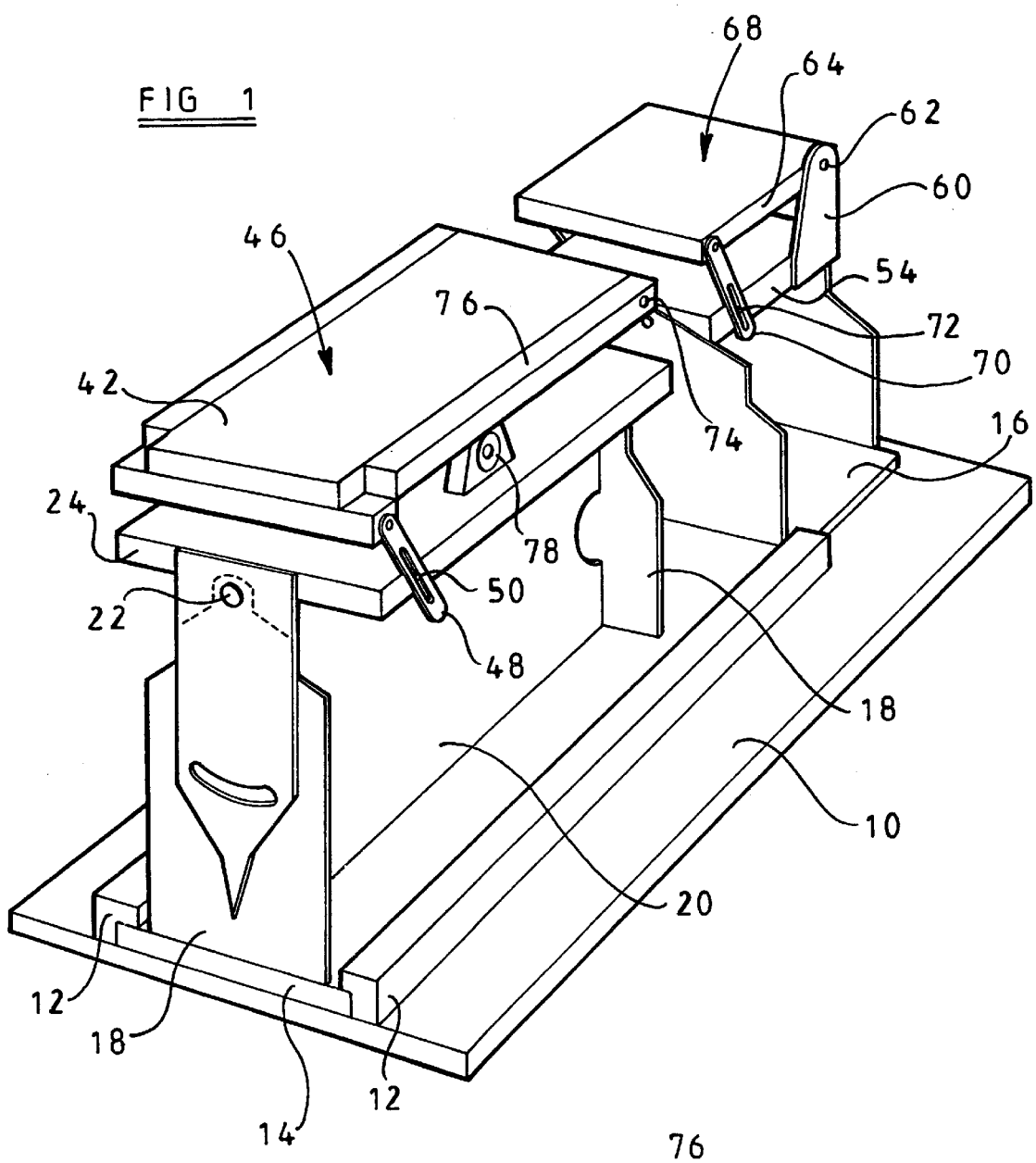
FIG. 1 is a perspective view illustrating an apparatus in accordance with an embodiment.
Figure 2:
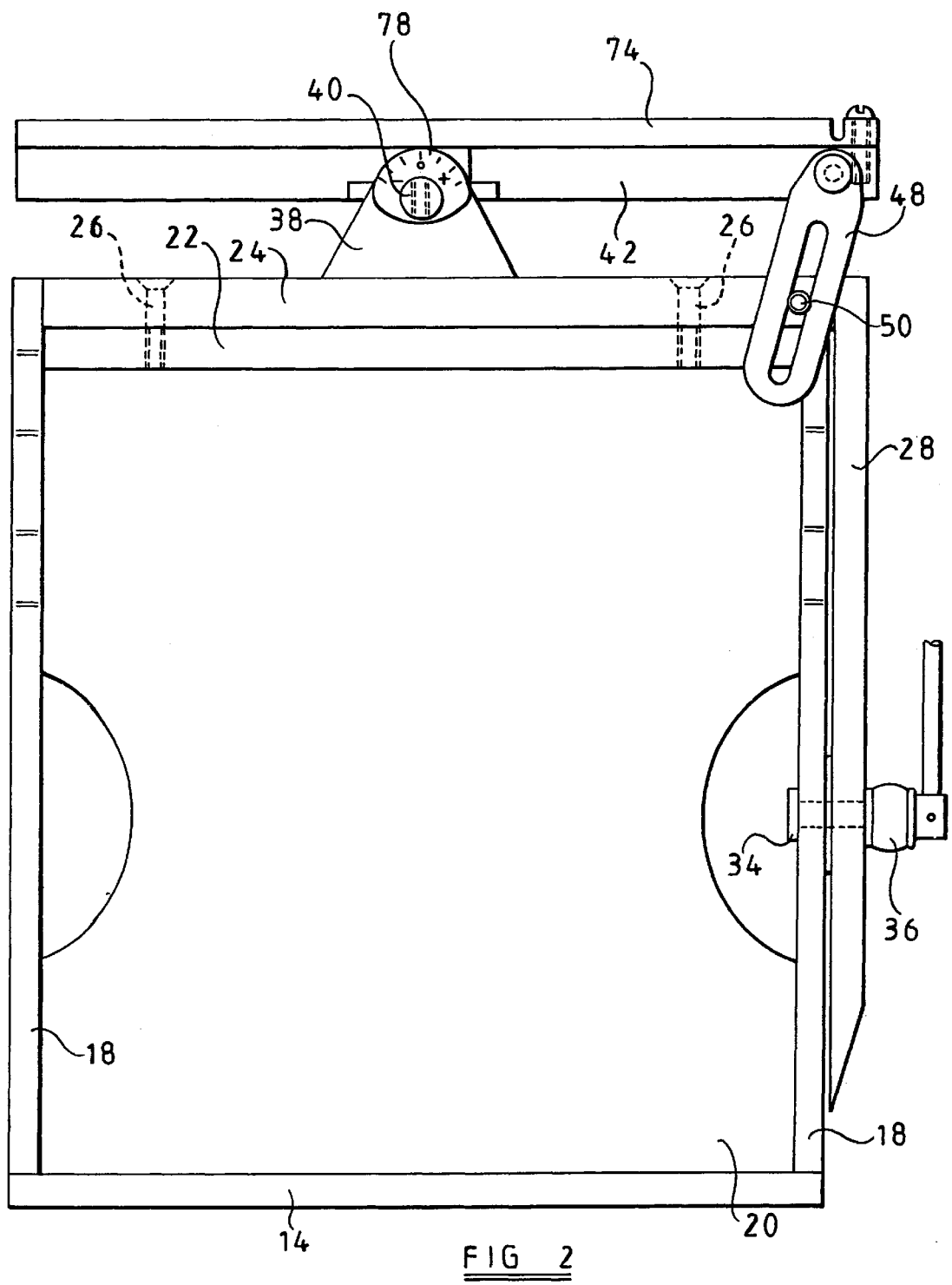
FIG. 2 is a side view illustrating part of the apparatus of FIG. 1.
Figure 4:
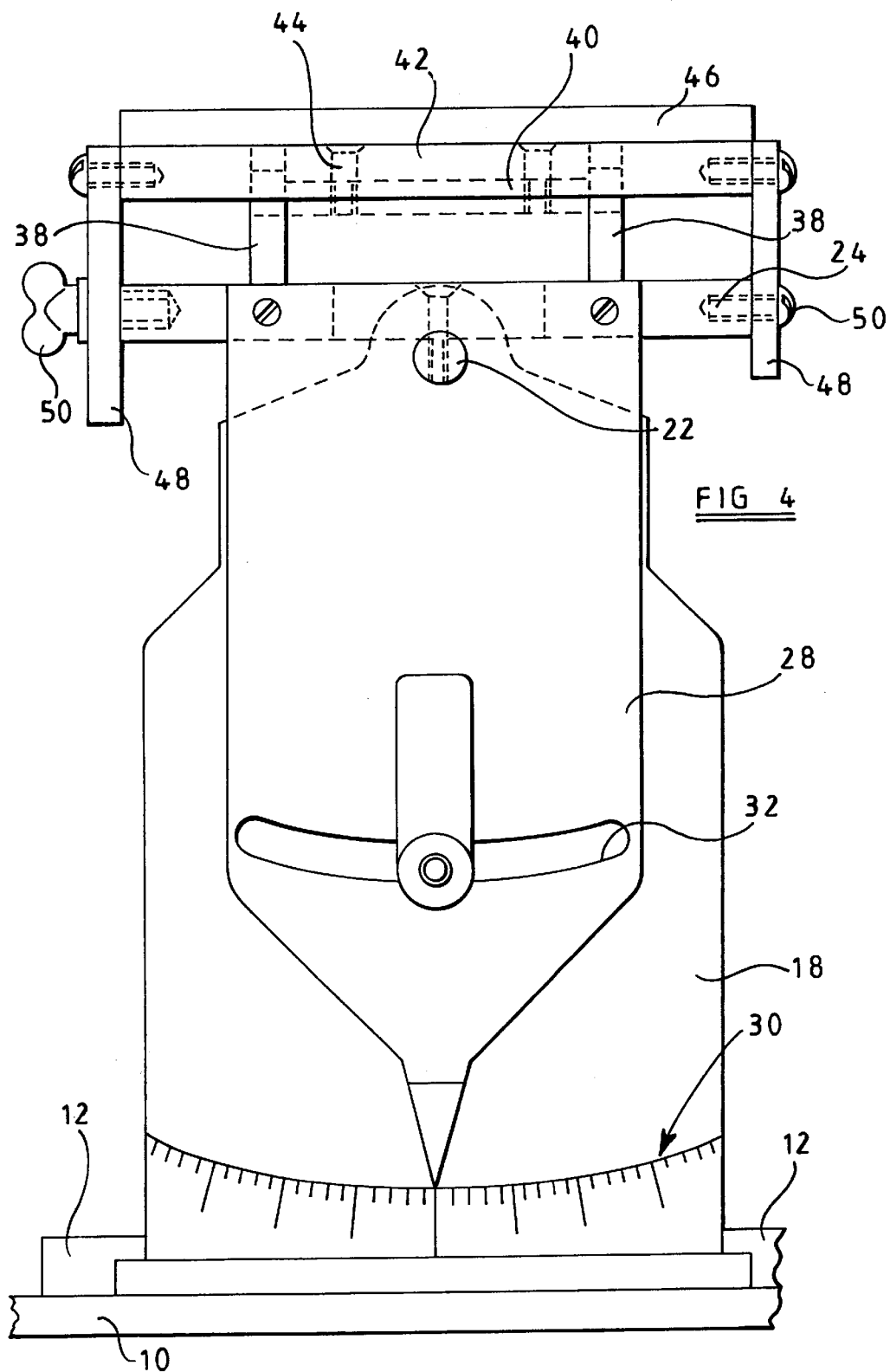
FIG. 4 is an end view of the apparatus.

As illustrated in FIGS. 1, 2 and 4, the first support arrangement includes a pair of end walls 18 which are mounted upon and carried by the first base plate 14, the end walls 18 being connected to one another by an interconnecting web 20 which act to ensure that the end walls 18 remain in a substantially vertical orientation even when a significant load is applied thereto. The upper ends of the end walls 18 are shaped so as to taper to a region of relatively small width which is provided with an opening through which a pivot member in the form of a rod 22 extends. The rod 22 carries a lower support member 24, the support member 24 being sewed to the rod 22 by means of screw-threaded bolts 26. The pivotal mounting of the rod 24 to the end walls 18 ensures that the lower support member 24 is pivotable about an axis which extends parallel to the longitudinal axis of the base plate 10.

A pointer 28 is rigidly secured to an end face of the lower support member 24, the pointer 28 tapering, at its lower end, to a point, the adjacent part of the end wall 18 being provided with a scale 30 thus allowing tile pointer 28 to be used in measuring the angle of the lower support member 24. The pointer 28 is further provided with an arcuate slot 32 through which a bolt 34 secured the adjacent end wall 18 extends. An appropriate internally screw-threaded nut 36 is secured to the bolt 34, and it will appropriate that tightening of the nut 36 and bolt 34 clamps the pointer 28 to the end wall 18, thus locking the lower support member 24 against angular movement about the pivot axis of the rod 22.

The lower support member 24 carries a pair of upstanding arms 38 which are aligned with one another, the arms 38 including aligned openings through which a pivot rod 40 extends, a first foot plate 42 being secured to the rod 40 by means of bolts 44. The fist foot plate 42 is provided with an appropriate covering material 46 which may simply be provided for comfort for the patient, or alternatively may be intended to deform in use to form a mould for use in producing an appropriate orthosis.

A plurality of linkage members 48 are pivotally mounted to the foot plate 42, the linkage members 48 each being provided with an axially extending slot through which a respective bolt 50 secured to the lower support member 24 is secured. One or more of the bolts 50 may be provided, at its outer end, with a bead which is shaped for manual adjustment. The provision of the linkage members 48 and bolts 50 act to stabilize the foot plate 42 and permit locking of the foot pate 42 in a desired position relative to the support member 24, after which measurements regarding the angle of the rear foot plate 42 may be taken. Conveniently, the slot of one of the linkage members 48 is provided with scale markings to permit measurement of the angle of the foot plate 42.

It will be appreciated that the foot plate 42 and covering 46 are pivotal in both the frontal plane, is being achieved by the pivotal mounting of the rod 22 and lower support member 24 to the end walls 18, and in the sagittal plane, this being achieved through the pivotal mounting of the foot plate 42 to the lower support member 24 through the rod 40. In a modification, the plate 42 may be mounted in such a manner that it is not pivotable about the rod 40 in which case the plate is only adjustable in the frontal plane. It is thought that, in practice, such a modification does not significantly alter the range of applications in which the apparatus can be used.

Figure 5:
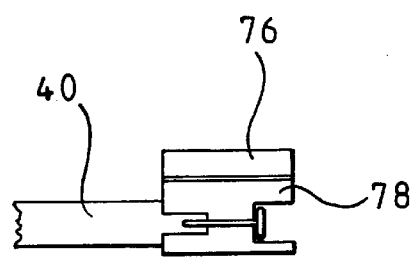
FIG. 5 is a view illustrating the cam arrangement of the apparatus.

As shown in FIG. 1, pivotally mounted to the foot plate 42 by a pivot pin 74 are a pair of side plates 76, the angles of which relative to the support member 24 can be adjusted by a cam arrangement 78 (see FIG. 5) to permit measurement of the displacement of the patient's first metatarsal complex, the selection of which side plate 76 to adjust being dependent upon whether the patient's left or right foot is being assessed. If desired, the pin 74 may be omitted, and instead the flexibility of the material used to permit deflection of the side plate(s), the material acting as a living hinge.

Figure 3:
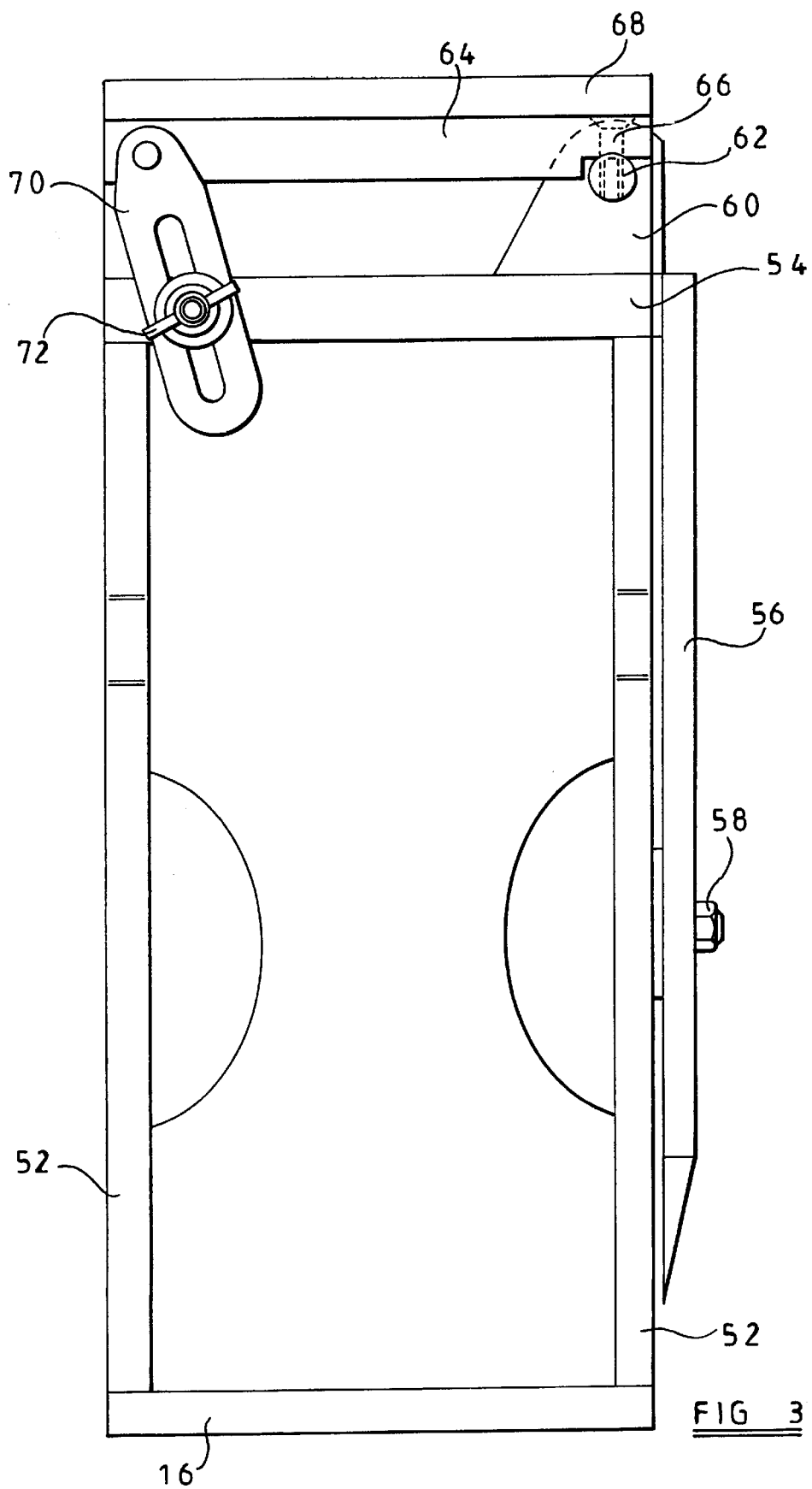
FIG. 3 is a side view illustrating another part of the apparatus.

The second support arrangement which is illustrated most clearly in FIG. 3 comprises a pair of end walls 52 which are secured to the base member 16 and are shaped in a manner similar to the end walls 18 of the first support arrangement. A lower support member 54 is pivotally mounted to the end walls 52 in a manner similar to that of the first support arrangement, a pointer 56 being secured to the lower support member 54, the pointer 56 being used in conjunction with a scale provided on part of the adjacent one of the end walls 18 to permit readings to be taken of the angle of the lower support member 54 relative to the base plate 10 about the axis of pivotal movement of the lower support member 54. The pointer 56 is provided with an arcuate slot through which a bolt (not shown) secured to the end wall 52 extends, a nut 58 engage the bolt to permit clamping of the pointer 56 to the end wall 52 to prevent movement of fie lower support member 54 when desired.

The lower support member 54 carries, at its end remote from the first support arrangement, a pair of support arms 60 which are provided with openings, aligned with one another, through which a pivot rod 62 extends. The pivot rod 62 carries a second foot plate 64, the foot plate 64 being secured to the pivot rod 62 by means of bolts 66. As with the first support arrangement, an appropriate covering 68 is provided over the foot plate 64, either for comfort or to permit moulding of an appropriate orthosis.

A pair of linkage members 70 are pivotally mounted upon the foot plate 64, the linkage members 70 each including an axially extending slot through which a bolt secured to the lower support member 54 extends, at least one of the bolts 72 being shaped to shaped to permit manual adjustment thereof to permit locking of the foot plate 64 against pivotal movement about the axis of the rod 62 relative to the lower support member 54.

It will be appreciated that the foot plate 64 is adjustable in both the frontal and sagittal planes, adjustment of the second foot plate 64 being totally independent of adjust of the first foot plate 42.

In use, a patient stands with one foot on an appropriate support block located adjacent the apparatus illustrated in the accompanying drawings, his other foot being located upon the fist and second foot plates 42, 64. Adjustment of the separation of the first and second foot plates 42, 64 is undertaken to allow for variations in the size of patient's feet.

The angles of the first and second foot plates 42, 64 and the appropriate side plate 76 are adjusted, in the frontal and sagittal planes as appropriate, until the patient's foot and lower limb are properly supported to permit correction of or compensation for foot and lower limb abnormalities, thereby adjusting the patient's stance. Once adjustment of the angles of the foot plates 42, 64 has been completed, the foot plates 42, 64 are secured in position by clamping the pointers 28, 56 to the adjacent end walls 18, 52 and by tightening of certain of the bolts 50, 72. Once the foot plates 42, 64 have been locked in position, measurements nay be taken regarding the angles of the foot plates 42, 64, and if appropriate, the coverings 46, 68 may be removed from the foot plates 42, 64 for use in manufacture of an appropriate orthosis for the patient. It will be appreciated that as the pointers 28, 56 are relatively long, the measurement of relatively small angles can be achieved to a high accuracy.

By providing the coverings 46, 68 with appropriate markings, it is also possible to assess misalignments of joints in the transverse direction of the base plate 10.

It is envisaged that in one particularly advantageous embodiment of the invention, the support step or block used to support the foot of the patient which is not being assessed using the apparatus may also act as a carrying case for the apparatus.

What is claimed is:

1. An apparatus for assessing and measuring, in three dimensions, foot and lower limb abnormalities comprising a rear plate intended to support a rear part of a patient's foot, in use, the rear plate being pivotable in both a frontal plane and a sagittal plane, a front plate intended to support a front part of the patient's foot the front plate being pivotable in the frontal plane independently of the rear plate, a side plate, the side plate being associated with and pivotally connected to the front plate, and an adjustment arrangement permitting adjustment of an angle of the side plate relative to the front plate in the sagittal plane.

2. An apparatus as claimed in claim 1, further comprising means for locking the front and rear plates and means permitting measurement of angles of the front and rear plates.

3. An apparatus as claimed in claim 2, wherein the means for locking comprise screw-threaded members adjustable to clamp the front and rear plates in position.

4. An apparatus as claimed in claim 2, wherein the means permitting measurement comprise pointers associated with the front and rear plates and moveable relative to associated scales.

5. An apparatus as claimed in claim 1, wherein the adjustment arrangement comprises a cam mechanism.

6. An apparatus as claimed in claim 1, further comprising an additional similar side plate.

7. An apparatus as claimed in claim 1, wherein the pivotal connection of the or each side plate to the front plate is achieved by means of a living hinge.

\* \* \* \* \*